(12) United States Patent
Tegels

(10) Patent No.: US 9,820,735 B2
(45) Date of Patent: Nov. 21, 2017

(54) LARGE BORE LOCATION DEVICE AND METHODS

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 719 days.

(21) Appl. No.: 13/675,889

(22) Filed: Nov. 13, 2012

(65) Prior Publication Data

US 2013/0123812 A1 May 16, 2013

Related U.S. Application Data

(60) Provisional application No. 61/560,507, filed on Nov. 16, 2011.

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0057* (2013.01); *A61B 2017/00663* (2013.01);
(Continued)

(58) Field of Classification Search
CPC . A61B 17/0482; A61B 17/0483; A61B 17/04; A61B 2017/00663; A61B 17/0468;
(Continued)

(56) References Cited

U.S. PATENT DOCUMENTS 3,470,875 A 10/1969 Johnson
5,431,666 A 7/1995 Sauer et al.
(Continued)

FOREIGN PATENT DOCUMENTS

EP 0818178 A2 1/1998
EP 1158907 A1 12/2001
(Continued)

OTHER PUBLICATIONS

Notification of Transmittal of the International Search Report and the Written Opinion of the International Searching Authority or the Declaration for International Application No. PCT/US2012/064768, dated Feb. 19, 2013, (18 pp.).
(Continued)

*Primary Examiner* — Christopher L Templeton
*Assistant Examiner* — Mikail Mannan
(74) *Attorney, Agent, or Firm* — Holland & Hart

(57) ABSTRACT

A vascular closure system includes a body portion, an anchor, at least one suture member, and a plurality of needles. The anchor assembly includes a hub and a wire assembly. The hub has at least one aperture defined in a sidewall thereof. The wire assembly includes an actuator member extending proximally through the body portion and hub, and at least one pre-formed wire having a free proximal end and a distal end that is connected to the actuator member. Withdrawing the actuator member extends the proximal end of the at least one pre-formed wire out of the at least one aperture to capture a portion of the vessel wall between the pre-formed wire and the body portion. The plurality of needles extend through the vessel wall adjacent to the vessel puncture and are configured to connect to the at least one suture member.

22 Claims, 14 Drawing Sheets

(51) Int. Cl.
*A61B 17/22* (2006.01)
*A61B 17/34* (2006.01)

(52) U.S. Cl.
CPC . *A61B 2017/047* (2013.01); *A61B 2017/0472* (2013.01); *A61B 2017/22042* (2013.01); *A61B 2017/22045* (2013.01); *A61B 2017/3484* (2013.01)

(58) Field of Classification Search
CPC .. A61B 2017/0472; A61B 2017/00637; A61B 2017/00496; A61B 2017/00641; A61B 17/0057; A61B 17/0469
USPC .......................................... 606/139–151, 232
See application file for complete search history.

(56) References Cited

U.S. PATENT DOCUMENTS

| | | | |
|---|---|---|---|
| 5,496,332 A * | 3/1996 | Sierra | A61B 17/0057 606/139 |
| 5,520,702 A | 5/1996 | Sauer et al. | |
| 5,562,686 A | 10/1996 | Sauer et al. | |
| 5,613,974 A | 3/1997 | Andreas et al. | |
| 5,643,292 A | 7/1997 | Hart | |
| 5,674,231 A | 10/1997 | Green et al. | |
| 5,700,273 A | 12/1997 | Buelna et al. | |
| 5,709,692 A | 1/1998 | Mollenauer et al. | |
| 5,728,114 A | 3/1998 | Evans et al. | |
| 5,766,183 A | 6/1998 | Sauer | |
| 5,860,990 A | 1/1999 | Nobles et al. | |
| 5,928,266 A * | 7/1999 | Kontos | A61B 17/0057 604/106 |
| 5,972,005 A | 10/1999 | Stalker et al. | |
| 6,036,699 A | 3/2000 | Andreas et al. | |
| 6,048,357 A | 4/2000 | Kontos | |
| 6,059,800 A | 5/2000 | Hart et al. | |
| 6,136,010 A * | 10/2000 | Modesitt | A61B 17/0057 606/139 |
| 6,355,050 B1 | 3/2002 | Andreas et al. | |
| 6,562,052 B2 | 5/2003 | Nobles et al. | |
| 6,623,509 B2 | 9/2003 | Ginn | |
| 6,641,592 B1 | 11/2003 | Sauer et al. | |
| 6,896,692 B2 | 5/2005 | Ginn et al. | |
| 6,911,034 B2 | 6/2005 | Nobles et al. | |
| 6,932,824 B1 | 8/2005 | Roop et al. | |
| 6,964,668 B2 | 11/2005 | Modesitt et al. | |
| 6,969,397 B2 | 11/2005 | Ginn | |
| 7,001,400 B1 | 2/2006 | Modesitt et al. | |
| 7,083,635 B2 | 8/2006 | Ginn | |
| 7,182,769 B2 * | 2/2007 | Ainsworth et al. | 606/142 |
| 7,235,087 B2 | 6/2007 | Modesitt et al. | |
| 7,361,183 B2 | 4/2008 | Ginn | |
| 7,390,328 B2 | 6/2008 | Modesitt | |
| 7,553,319 B2 | 6/2009 | Bagaoisan et al. | |
| 7,601,161 B1 | 10/2009 | Nobles et al. | |
| 7,621,937 B2 | 11/2009 | Pipenhagen et al. | |
| 7,686,821 B2 | 3/2010 | Hathaway et al. | |
| 7,731,726 B2 | 6/2010 | Belhe et al. | |
| 7,744,610 B2 | 6/2010 | Hausen | |
| 7,752,853 B2 | 7/2010 | Singh et al. | |
| 7,753,933 B2 | 7/2010 | Ginn et al. | |
| 7,837,696 B2 | 11/2010 | Modesitt et al. | |
| 7,842,047 B2 | 11/2010 | Modesitt et al. | |
| 7,842,048 B2 | 11/2010 | Ma | |
| 7,842,068 B2 * | 11/2010 | Ginn | A61B 17/0057 606/213 |
| 7,846,170 B2 | 12/2010 | Modesitt et al. | |
| 7,850,701 B2 | 12/2010 | Modesitt et al. | |
| 7,883,517 B2 | 2/2011 | Pantages et al. | |
| 7,985,240 B2 | 7/2011 | Bagaoisan et al. | |
| 8,016,794 B2 * | 9/2011 | Rosenberg | A61M 25/04 604/174 |
| 8,029,476 B2 | 10/2011 | Rosenberg et al. | |
| 8,048,092 B2 | 11/2011 | Modesitt et al. | |
| 8,083,768 B2 | 12/2011 | Ginn et al. | |
| 8,192,456 B2 | 6/2012 | Holman et al. | |
| 2005/0059982 A1 * | 3/2005 | Zung | A61B 17/0057 606/144 |
| 2005/0085854 A1 | 4/2005 | Ginn | |
| 2006/0212071 A1 | 9/2006 | Ginn et al. | |
| 2008/0065151 A1 | 3/2008 | Ginn | |
| 2008/0097479 A1 * | 4/2008 | Boehlke et al. | 606/144 |
| 2009/0099578 A1 | 4/2009 | Heneveld et al. | |
| 2009/0306685 A1 | 12/2009 | Fill | |
| 2010/0042118 A1 | 2/2010 | Garrison et al. | |
| 2011/0071567 A1 | 3/2011 | Modesitt et al. | |
| 2012/0296373 A1 * | 11/2012 | Roorda | A61B 17/0057 606/213 |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 | 2/1997 |
| WO | 0051498 | 9/2000 |
| WO | 0078226 A1 | 12/2000 |
| WO | 2010081106 A1 | 7/2010 |

OTHER PUBLICATIONS

Notification of Transmittal of the International Search Report and the Written Opinion of the International Searching Authority or the Declaration for International Application No. PCT/US2012/066012, dated Feb. 19, 2013, (17 pp.).

Notification of Transmittal of the International Search Report and the Written Opinion of the International Searching Authority, or the Declaration for International Application No. PCT/US2012/064770, dated Feb. 19, 2013, (16 pp.).

PCT Communication Relating to the Results of the Partial International Search for International Application No. PCT/US2012/041196, dated Sep. 11, 2012.

U.S. Appl. No. 61/494,345, filed Jun. 7, 2011.

* cited by examiner

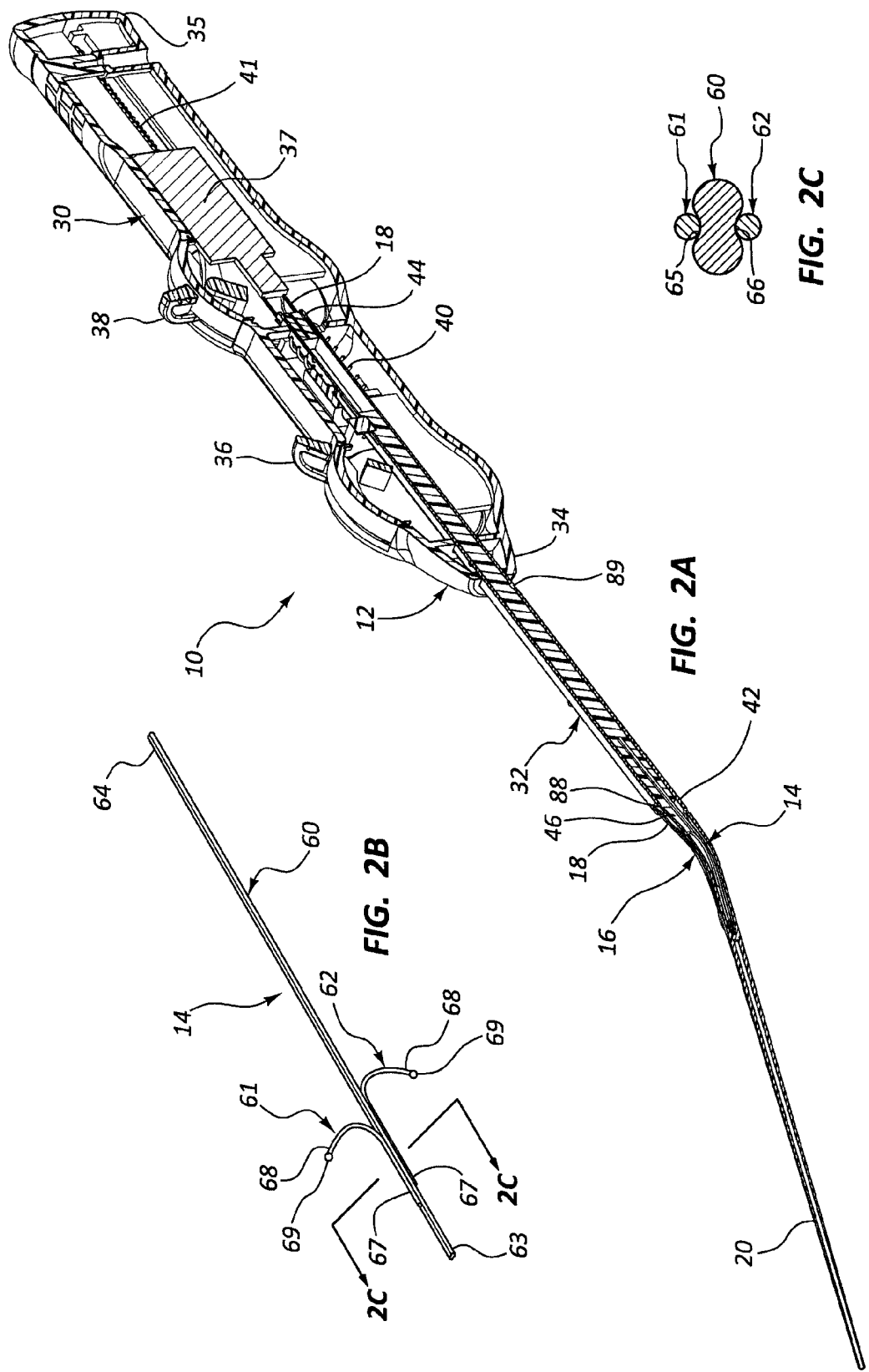

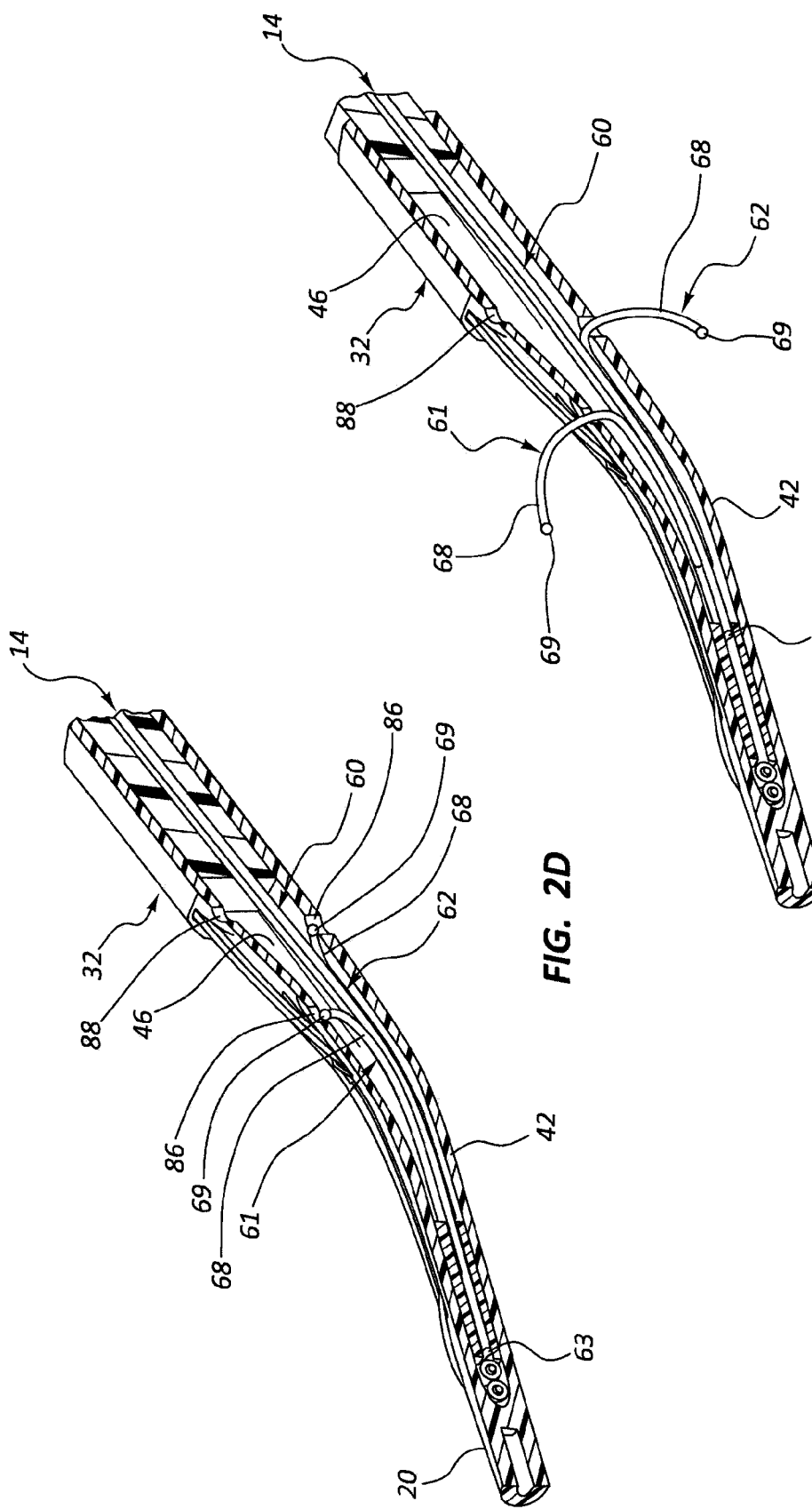

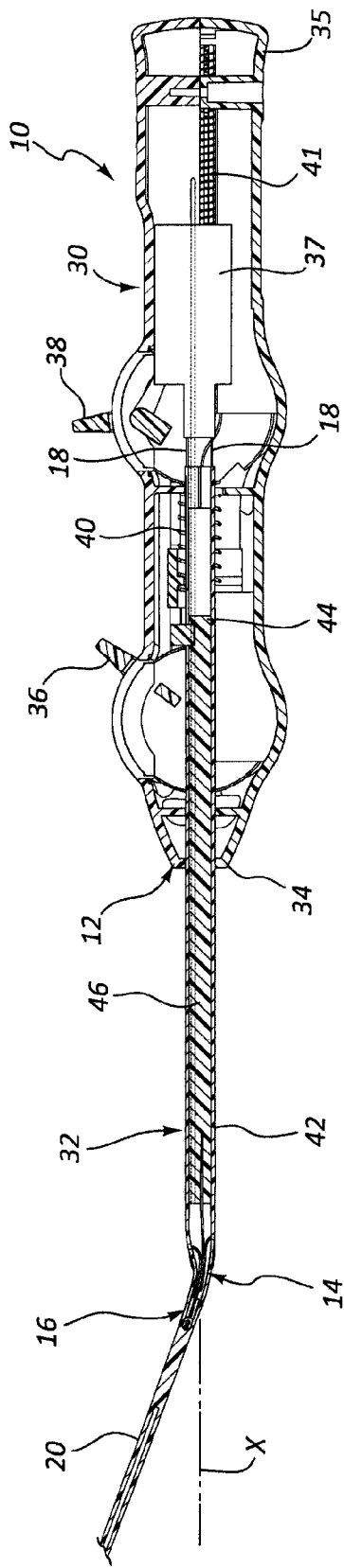
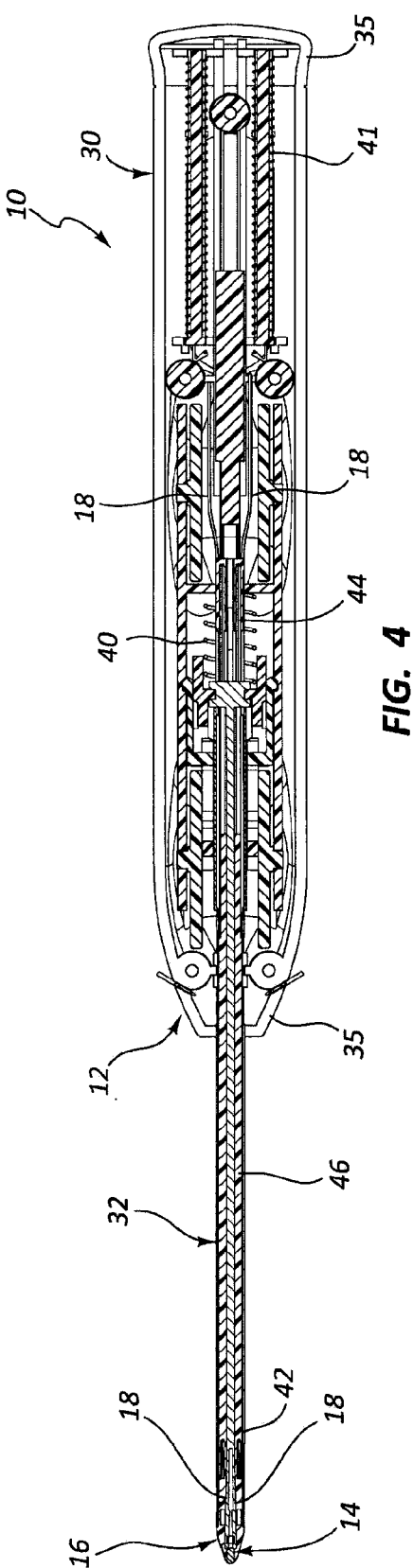
FIG. 3
FIG. 4

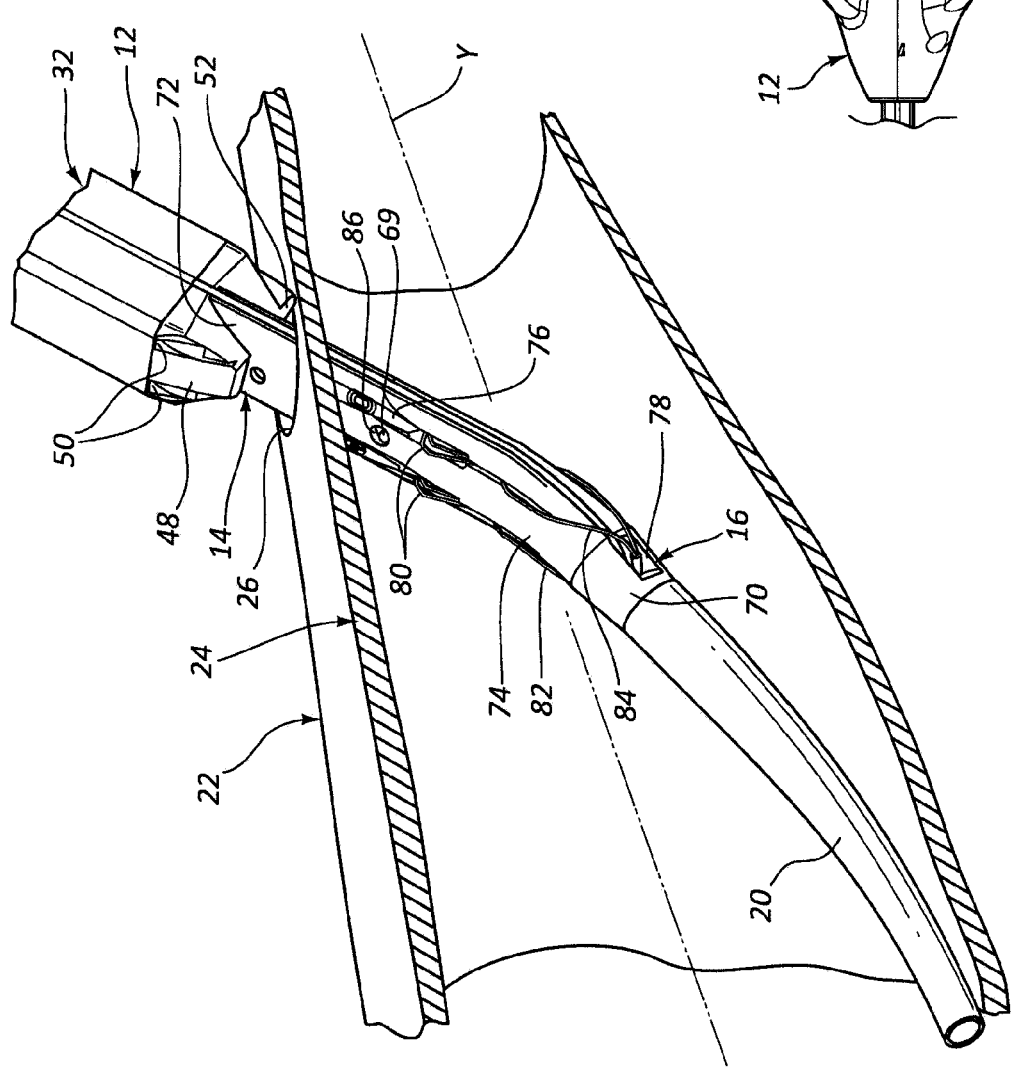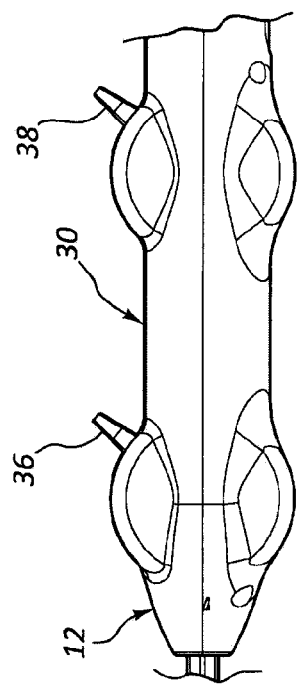
FIG. 5A
FIG. 5B

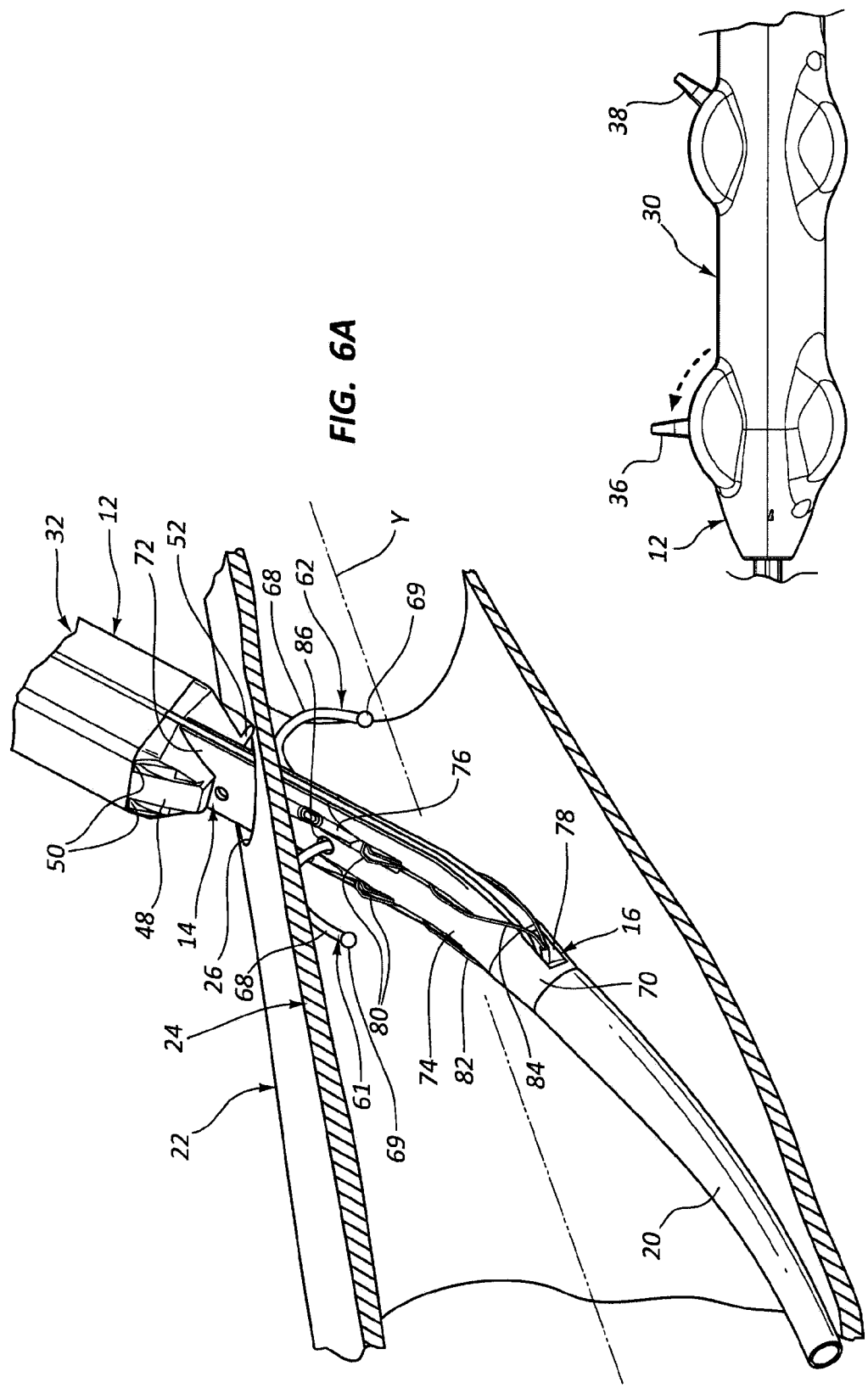

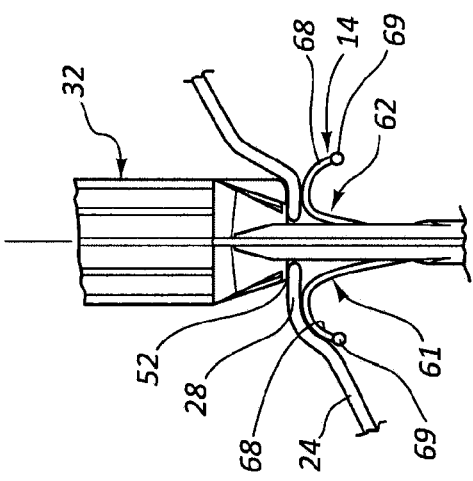
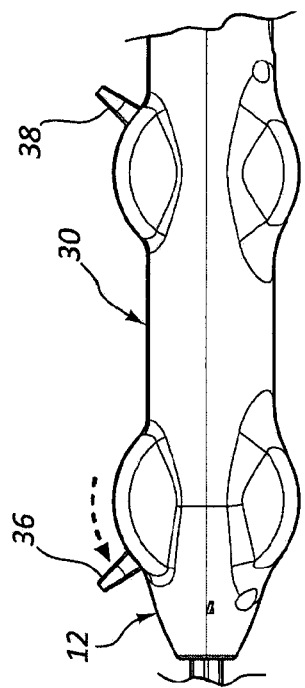
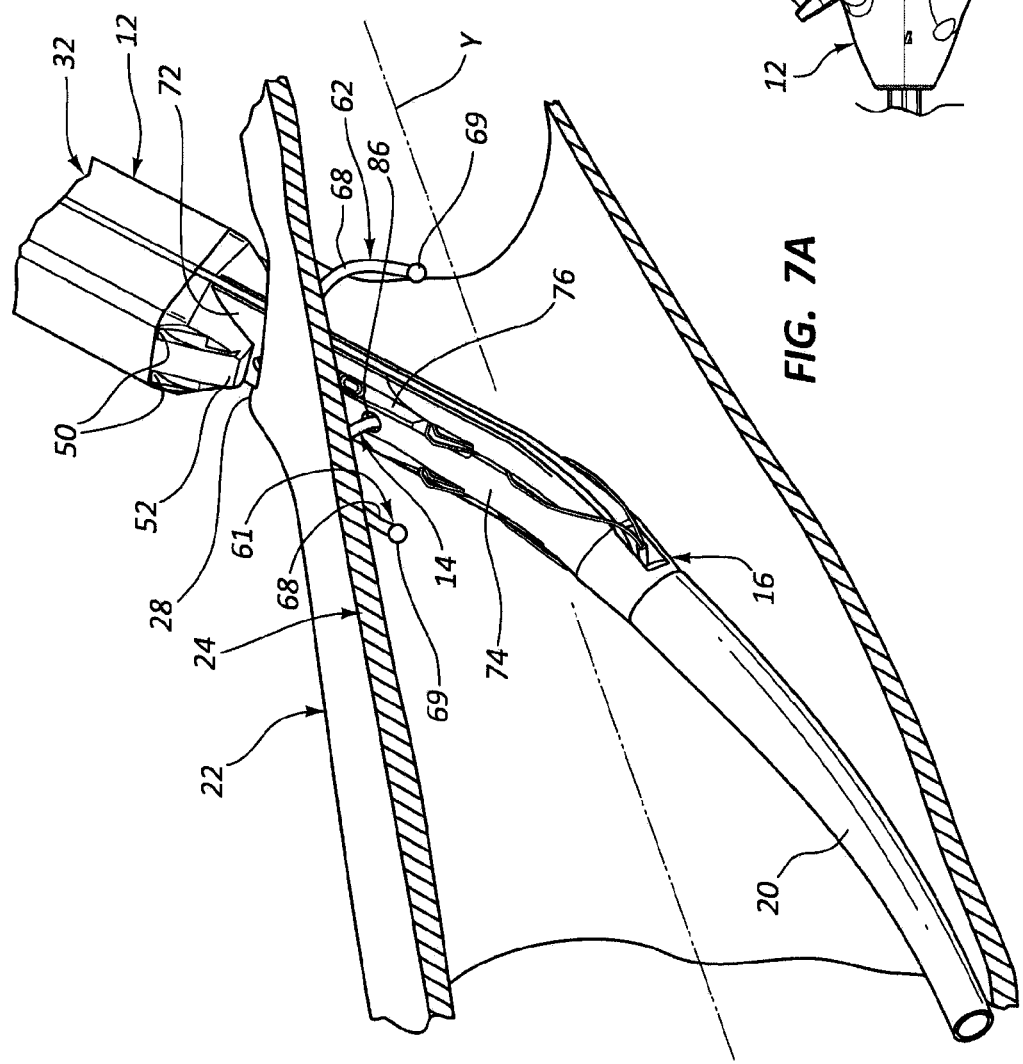
FIG. 7C
FIG. 7B
FIG. 7A

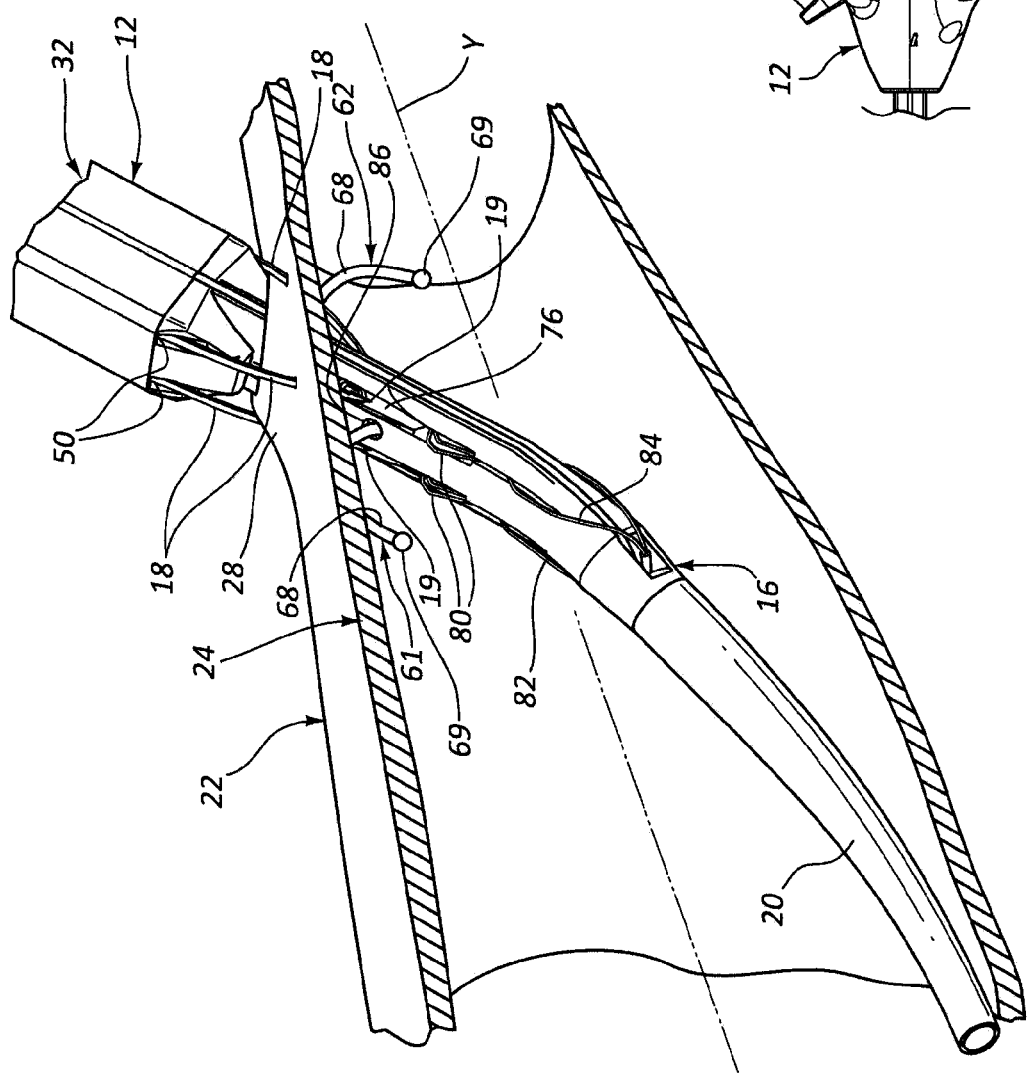
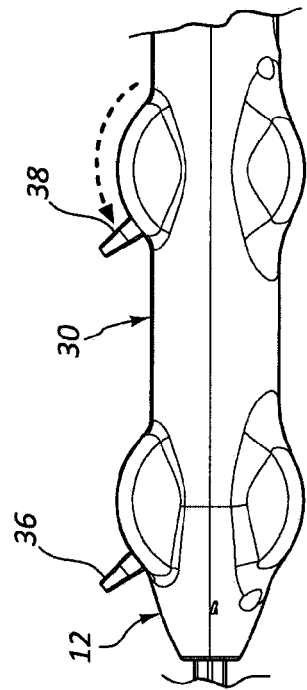
FIG. 8A
FIG. 8B

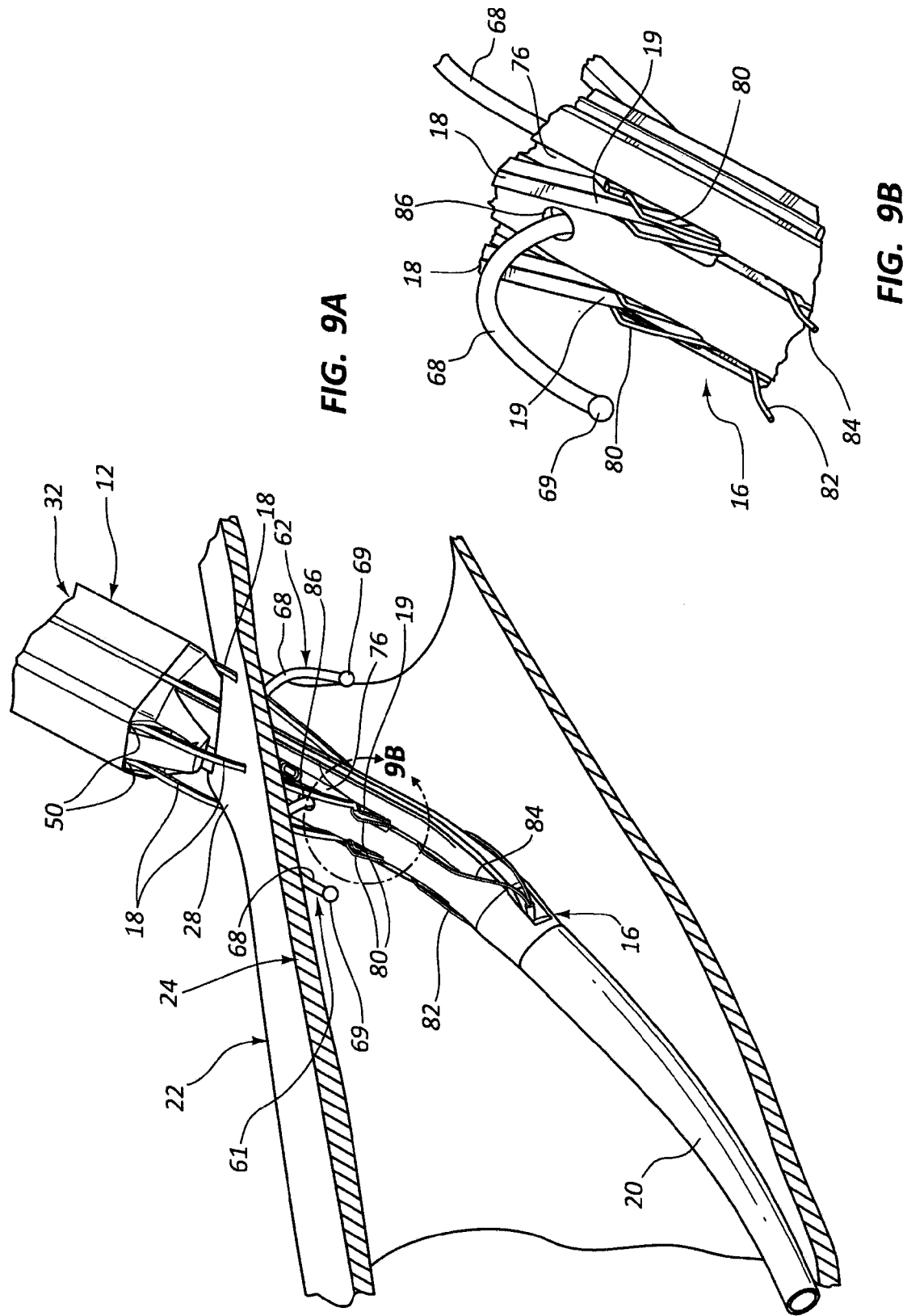

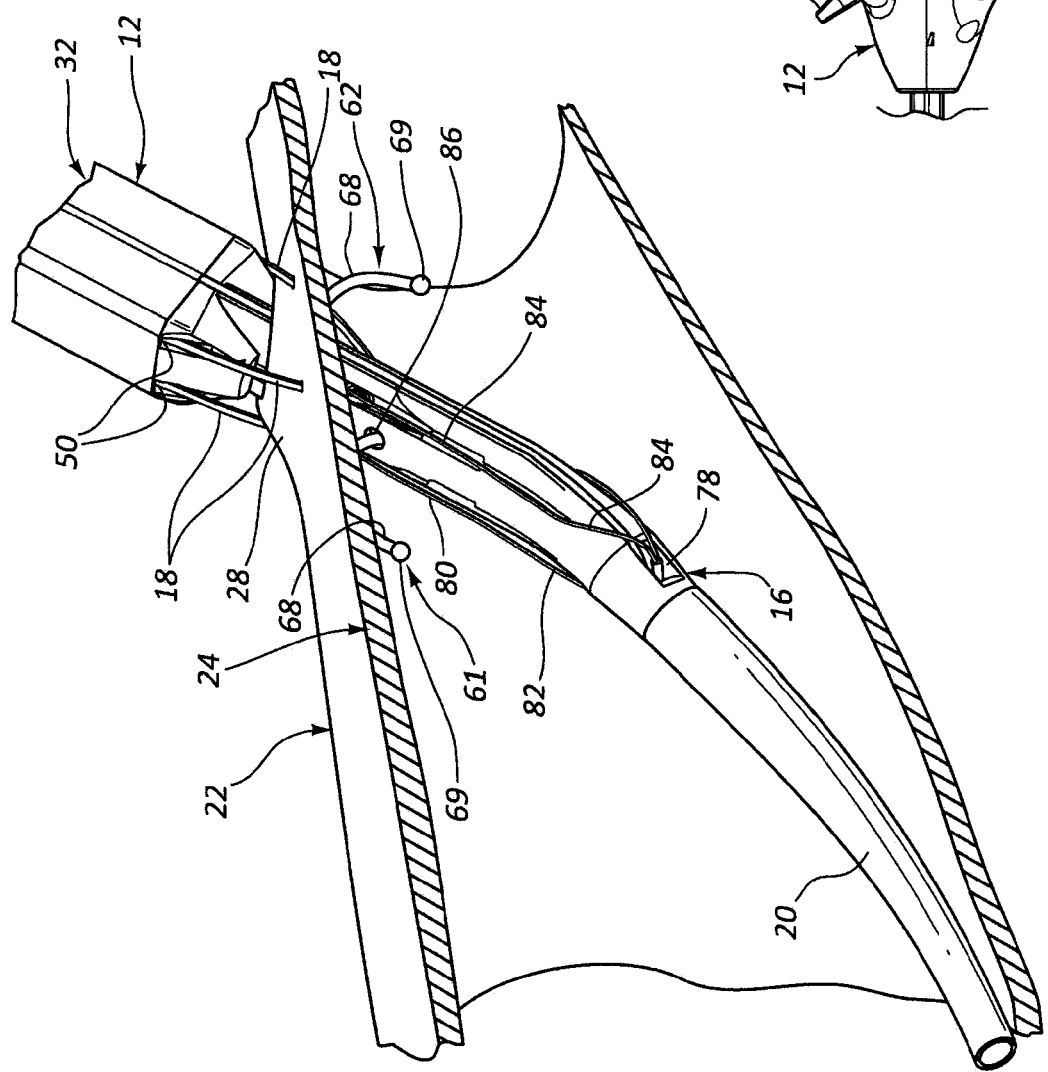
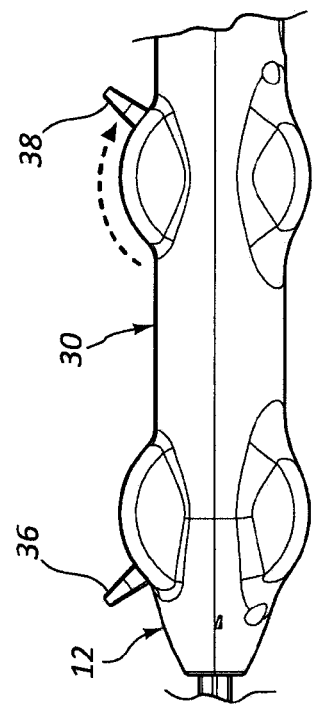
FIG. 10A
FIG. 10B

LARGE BORE LOCATION DEVICE AND METHODS

RELATED APPLICATION

This application claims the benefit of U.S. Provisional App. No. 61/560,507, filed 16 Nov. 2011, which is hereby incorporated by reference herein in its entirety.

TECHNICAL FIELD

The present disclosure relates to closure devices, and more specifically relates to closure devices that place sutures across an opening in a vessel wall.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is further a need to provide a suturing device that minimizes the invasiveness of the suturing procedure.

SUMMARY

One aspect of the present disclosure relates to a vascular closure system that includes a body portion, an anchor, at least one suture member, and a plurality of needles. The anchor assembly is positionable through a vessel puncture in a wall of a vessel and includes a hub and a wire assembly. The hub has at least one aperture defined in a sidewall thereof. The wire assembly includes an actuator member extending proximally through the body portion and hub, and at least one pre-formed wire having a free proximal end and a distal end that is connected to the actuator member. Withdrawing the actuator member extends the proximal end of the at least one pre-formed wire out of the at least one aperture to capture a portion of the vessel wall between the pre-formed wire and the body portion. The at least one suture member is positioned distal of the body portion. The plurality of needles extend through the portion of the vessel wall adjacent to the vessel puncture and are configured to connect to the at least one suture member. Withdrawal of the plurality of needles through the portion of the vessel wall positions the at least one suture member through the portion of the vessel wall.

The pre-formed wire may comprise a J-shape. The wire assembly may include first and second pre-formed wires arranged on opposite sides of the actuator member. The proximal end of the at least one pre-formed wire may be pre-positioned in the at least one aperture. The at least one pre-formed wire may include a contact tip at the proximal end, wherein the contact tip has a bulbous shape. The proximal end of the at least one pre-formed wire may extend radially outward upon withdrawal of the actuator member. The proximal end of the first pre-formed wire may extend further proximally than the proximal end of the second pre-formed wire. The at least one pre-formed wire may be welded to the actuator member. The body portion may include a handle assembly at a proximal end thereof, and first and second actuators operable to actuate the actuator member and the needles, respectively.

Another aspect of the present disclosure relates to a vascular closure device that includes a body portion, a hub, a wire assembly, first and second suture members, and first and second pairs of needles. The hub is positionable through a puncture in a vessel and has at least one aperture defined in a sidewall thereof. The wire assembly includes an actuator wire extending through the body portion and hub, and at least one anchor wire having a distal end connected to the actuator wire and a proximal end that extends out of the at least one aperture to capture a portion of a wall of the vessel between the pre-formed wire and the body portion upon withdrawal of the actuator wire. The first and second suture members are positioned within the vessel. The first and second pairs of needles are operable to advance through the portion of the vessel adjacent to the puncture, connect to the first and second suture members, and be withdrawn through the portion of the vessel to position the first and second suture members through the portion of the vessel.

The at least one anchor wire may include first and second anchor wires configured to extend through first and second apertures defined in the sidewall of the hub. The vascular closure device may include a blood location port positioned proximal of the at least one aperture. The pre-formed wire may comprise a J-shape when in a rest position. The actuator wire may include at least one groove sized to receive the distal end of the pre-formed wire. The distal end of the pre-formed wire may be welded within the at least one groove.

A further aspect of the present disclosure relates to a method of positioning sutures across a vascular opening in a vessel wall. The method includes providing a vascular closure device having a body portion, an anchor assembly, at least one length of suture, and a plurality of needles, wherein the anchor assembly includes a hub, an actuator wire, and a pre-formed wire having a distal end connected to the actuator wire. The method further includes inserting the anchor assembly and at least one length of suture through the vascular opening, withdrawing the actuator wire to advance a proximal end of the pre-formed wire through a sidewall of the hub, capturing a portion of the vessel wall between the pre-formed wire and a distal end of the body portion, and advancing the plurality of needles through the portion of the vessel wall adjacent to the vascular opening. The method also includes connecting the plurality of needles to the at least one length of suture, withdrawing the plurality of needles to position the at least one length of suture through the vessel wall adjacent to the vascular opening, advancing the actuator wire to move the pre-formed wire into the hub, and removing the anchor assembly through the vascular opening.

The method may also include providing a plurality of pre-formed wires that each extend through a separate wire aperture in the sidewall of the hub. Advancing a proximal end of the pre-formed wire may position a bend portion of the pre-formed wire in contact with the vessel wall. Advancing the actuator wire to move the pre-formed wire into the hub may include retracting all but a proximal tip of the pre-formed wire into the hub. The method may include maintaining a generally linear shape in the pre-formed wire prior to advancing the proximal end of the pre-formed wire through the sidewall of the hub, and providing a contoured shape in the pre-formed wire after advancing the proximal end through the sidewall of the hub.

The foregoing and other features, utilities, and advantages of the invention will be apparent from the following detailed description of the invention with reference to the accompanying drawings.

BRIEF DESCRIPTION OF THE DRAWINGS

FIG. 2A is a perspective cross-sectional view of the vascular closure system of FIG. 1A taken along cross-section indicators 2-2.

FIG. 2B is a perspective view of an anchor assembly of the vascular closure system of FIG. 2A.

FIG. 2C is a cross-sectional view of the anchor assembly of FIG. 2B taken along cross-section indicators 2C-2C.

FIG. 2D is a close-up view of a distal end portion of the vascular closure system of FIG. 2A with the anchor wires in a retracted position.

FIG. 2E is a close-up view of the distal end portion of the vascular closure system of FIG. 2A with the anchor wires moved into an expanded position.

FIG. 3 is a side cross-sectional view of the vascular closure system of FIG. 2A.

FIG. 4 is side cross-sectional view of the vascular closure system of FIG. 1A taken along cross-section indicators 4-4.

FIG. 5A is a perspective view of a distal end portion of the vascular closure system of FIG. 1 extending through a vessel puncture.

FIG. 5B is a side view of a handle portion of the vascular closure system of FIG. 1 with actuator positions representing a state of the distal end portion shown in FIG. 5A.

FIG. 6A is a perspective view of the distal end portion of the vascular closure system of FIG. 5A with the anchor in an extended position.

FIG. 6B shows actuator positions of the handle portion representing a state of the distal end portion shown in FIG. 6A.

FIG. 7A is a perspective view of the distal end portion of the vascular closure system of FIG. 6A with a portion of the vessel wall captured between the anchor and a body portion of the vascular closure system.

FIG. 7B shows actuator positions of the handle portion representing a state of the distal end portion shown in FIG. 7A.

FIG. 7C is a side view of the distal end portion of the vascular closure system of FIG. 7A.

FIG. 8A is a perspective view of the distal end portion of the vascular closure system of FIG. 7A with needles extending through the vessel wall.

FIG. 8B shows actuator positions of the handle portion representing a state of the distal end portion shown in FIG. 8A.

FIG. 9A is a perspective view of the distal end portion of the vascular closure system of FIG. 8A with the needles connected to sutures within the vessel.

FIG. 9B is a detailed inset showing connection of the needles to the sutures in FIG. 9A.

FIG. 10A is a perspective view of the distal end portion of the vascular closure system of FIG. 9A with the needles retracted partially.

FIG. 10B shows actuator positions of the handle portion representing a state of the distal end portion shown in FIG. 10A.

DETAILED DESCRIPTION

Figure 1:
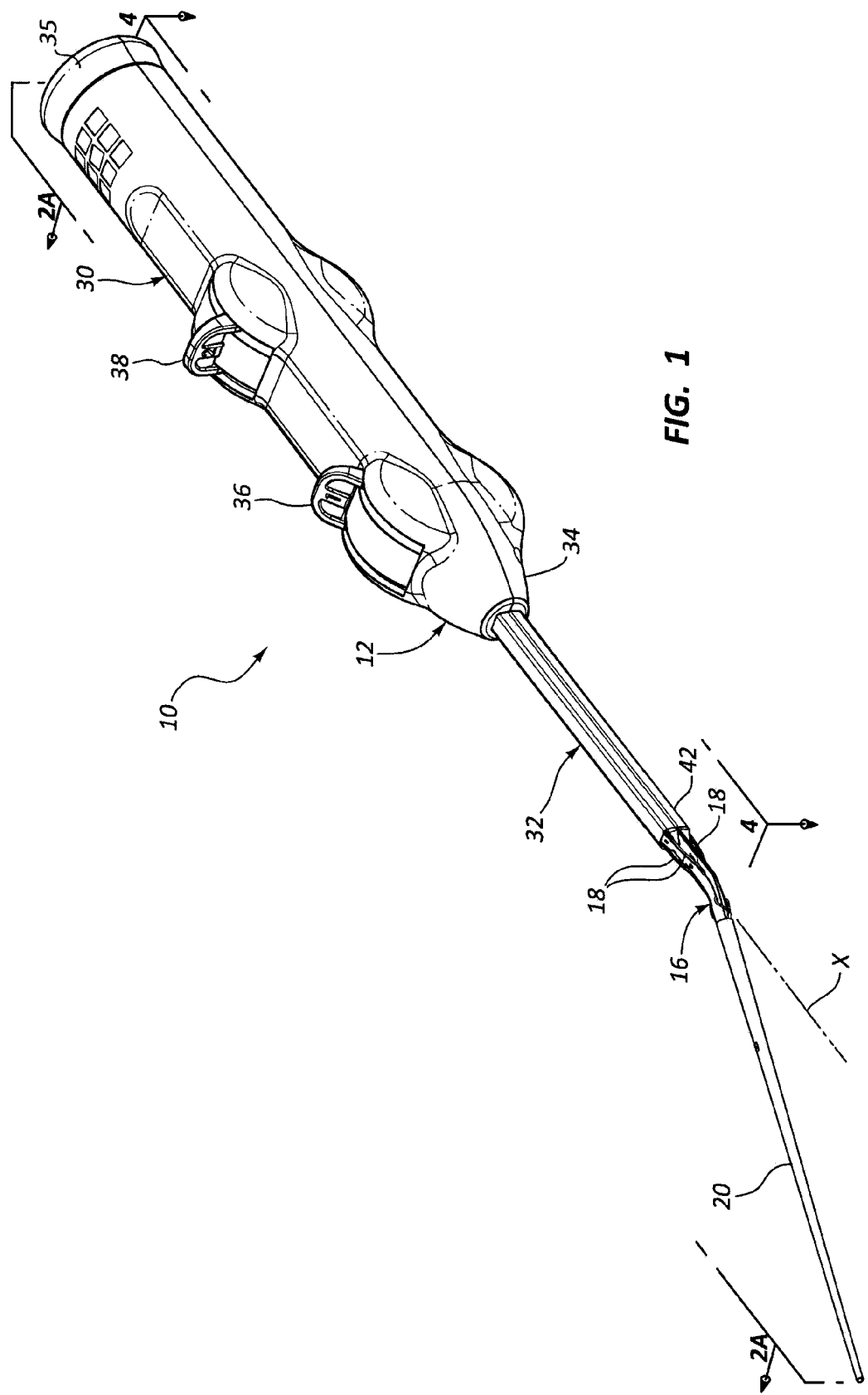
FIG. 1 is a perspective view of an example vascular closure system in accordance with the present disclosure.

The present disclosure is directed to an anchor assembly for use with a device that places at least one suture across a wound (e.g., a puncture in a vessel). In one embodiment, the device is adapted and configured to place a pair of sutures across an opening in a wall of the vessel. The present disclosure contemplates that a medical procedure will be performed through a sheath that is inserted through the opening in the vessel wall. The sheath provides access to the inside of the vessel. The device may be used prior to the sheath being inserted through the opening or after the medical procedure has been completed and the sheath removed. The device deploys at least one suture across the vessel opening by inserting a plurality of needles through the vessel wall adjacent to the opening. The needles grasp lengths of suture held by the device within the vessel, and withdrawing the needles pulls the lengths of suture through the vessel wall. The sutures may be subsequently used to close the opening. One use of the device is to place at least one suture through the vessel wall, wherein the suture is later used to close a puncture in the vessel wall (e.g., a puncture in a femoral artery incurred during a catheter based procedure).

The anchor assembly may include an actuator wire and an anchor wire that is connected to the actuator wire at a distal end of the anchor wire. A proximal end of the anchor wire moves into and out of apertures formed in a sidewall of a hub structure upon advancing and retracting the actuator wire axially along a length of the device. The anchor wire, when extending out of the hub, contacts an inner surface of the vessel wall to provide an anchor function for the device. The anchor wire, when retracted into the hub, permits the device to be move into and out of the vessel puncture.

The anchor assembly may include a plurality of anchor wires connected to the actuator wire. The anchor wires may be connected to the actuator wire at spaced apart locations along a length of the actuator wire. The different axial positions of the anchor wires, when in the expanded positions, may help account for an insertion angle of the device into the vessel. The anchor wires may have a pre-formed shape, such as, for example, a J-shape or C-shape when in a rest position. The pre-formed shape may provide a contoured surface that contacts the inner surface of the vessel when the anchor wires are in the expanded position.

A proximal end of the actuator wire may extend proximally to a handle or housing portion of the device where the proximal end is actuated to axially advance and retract the actuator wire. The actuator wire may be constructed to provide an improved interface with the anchor wires. In one example, the actuator wire has a cross-sectional shape with one or more grooves or recesses that provides increased surface contact with the anchor wires that are positioned therein. The anchor wires may be connected to the actuator wire with a weld (e.g., laser, TIG, plasma, Nd-Yag, or e-beam weld).

The anchor assembly may be used to capture and hold a portion of the vessel wall during insertion of a plurality of needles through the vessel wall and retraction of the needles to pull lengths of suture through the vessel wall. The anchor assembly may be configured to help reduce an overall profile of the device while providing the same or improved anchoring function as compared to other larger profile anchoring devices that result in larger profile devices.

Referring now to FIGS. 1-4, an example vascular closure system 10 is shown including a body portion 12, an anchor assembly 14, a suture carrying portion 16, a plurality of needles 18, and a distal locator tip 20. The body portion 12 may include a handle 30 and a delivery portion 32. The anchor assembly 14 may be movable between expanded and retracted positions relative to the body portion 12 and suture carrying portion 16. The needles 18 are operable to move between withdrawn positions within the body portion 12, and extended positions protruding through a vessel wall. The needles may be used to grasp lengths of suture carried by the suture carrying portion 16 and, when withdrawn, pull the lengths of suture through the vessel wall adjacent to the vessel puncture. Operation of the vascular closure system 10 is shown and described in further detail below related to FIGS. 5A-13.

The handle 30 of the body portion 12 includes distal and proximal ends 34, 35, first and second actuators 36, 38, and first and second biasing members 40, 41 (see FIGS. 1 and 2A). The first and second actuators 36, 38 may be pivotally mounted to the handle 30. Operation of the first actuator 36 moves the anchor assembly 14 between retracted and extended positions. Typically, the anchor assembly 14 maintains the retracted position while advancing the vascular closure system 10 through a vessel wall. The vascular closure system 10 may have its smallest outer profile when the anchor assembly 14 is in the retracted position to promote insertion through the vessel puncture. The first actuator 36 is rotated forward to expand or extend the anchor assembly 14 into a position that limits removal of the vascular closure system 10 from the vessel (see FIG. 6A).

The anchor assembly 14 may be movable axially relative to the body portion 12 and suture carrying portion 16. Operation of the first actuator 36 through its rotation path in a forward or advancing direction moves the anchor assembly 14 between retracted and expanded positions (see FIGS. 6A-7B). Operation of the first actuator 36 through its rotation path in the rearward or withdrawal direction moves the anchor assembly between expanded and retracted positions (see FIGS. 12A-B).

The second actuator 38 is operable to move the needles 18 between withdrawn and extended positions. The needles 18, when in a withdrawn position, may be completely recessed within the body portion 12. Operation of the second actuator 38 (i.e., rotation to a forward rotated position) advances the needles 18 distally out of the body portion 12 and through a vessel wall (see FIGS. 8A-B). The needles 18 include distal needle tips 19 (see FIGS. 8A and 9A-B) that connect to first and second sutures 82, 84 carried by the suture carrying portion 16 (see FIGS. 9A-B). Once the needles 18 are connected to the first and second sutures 82, 84, the second actuator 38 is operated to withdraw the needles 18 back into the body portion 12 (see FIGS. 10A-B). Moving the needles 18 proximally pulls the sutures through the vessel wall. Removing the vascular closure system 10 from the vessel exposes the sutures outside of the patient for handling by the operator.

Referring to FIGS. 2A and 3, the body portion 12 may include first and second biasing members 40, 41 and other mechanical features that provide operation of the first and second actuators 36, 38. The first and second biasing members 40, 41 may bias the first and second actuators 36, 38, respectively, into a certain rotated position (e.g., to a rearward rotated position). In one example, the handle 30 includes a needle carrier 37 to which the plurality of needles 18 are mounted at their proximal end (see FIGS. 2A and 3). Actuating the second actuator 38 may advance and withdraw the needle carrier 37 within the handle 30 and relative to the delivery portion 32 of the body portion 12.

As shown in FIGS. 4-5A, the delivery portion 32 of the body portion 12 includes distal and proximal ends 42, 44, respectively, a hollow interior 46, a plurality of needle openings 50 at the distal end 42 (see FIG. 5A), and a distal end surface 52. The proximal end 44 of the delivery portion 32 is mounted to the handle 30. The suture carrying portion 16 extends from the distal end 42 of the delivery portion 32. Portions of the anchor assembly 14, needles 18, and first and second actuators 36, 38 may be mounted within the hollow interior 46 of the delivery portion 32 (see FIG. 3). Portions of the anchor assembly 14 may extend through wire apertures 86 when the anchor assembly 14 moves between retracted and expanded positions. The needles may advance and withdraw through the needle openings 50.

The distal end surface 52 may define a contact surface against which a portion of the vessel contacts when captured between the body portion 12 and portions of the anchor assembly 14. The distal end surface 52 (see FIG. 5A) may include a generally flat or planar portion that extends generally perpendicular to a longitudinal axis X of the body portion 12 (see FIG. 3).

The anchor assembly 14 is moveable between a retracted position (see FIGS. 1, 2A, and 3-5A) and an expanded or extended position (see FIGS. 6A, 7A and 8A). While in the retracted position, the vascular closure system 10 has a reduced profile that permits insertion of the anchor assembly 14 through a tissue puncture. Upon actuation into an expanded or extended position, the anchor assembly 14 resists removal of the vascular closure system 10 back through the tissue puncture.

The anchor assembly 14 includes an actuator wire 60 and first and second anchor wires 61, 62 (also referred to as pre-formed wires) (see FIGS. 1-2C). The actuator wire 60 includes distal and proximal ends 63, 64, and may also include first and second grooves 65, 66. The distal end 63 is positioned distal of the distal end surface 52 of the body portion 12. The proximal end 64 extends proximally to the handle 30 for actuation by the first actuator 36. The first and second groove 65, 66 may be configured to receive the first and second anchor wires 61, 62 to provide improved contact therebetween. The first and second anchor wires 61, 62 may be connected to the actuator wire 60 using, for example, welding, adhesives, or other bonding methods.

The first and second anchor wires 61, 62 may each have distal and proximal ends 67, 68. The distal ends 67 are connected to the actuator wire 60. The proximal ends 68 are free ends and move into and out of the suture carrying portion 16 to provide an anchoring structure that contacts an inner surface of the vessel.

At least a portion of the first and second anchor wires 61, 62 extend radially outward and in a rearward direction from the suture carrying portion 16 (also referred to herein as a hub). The suture carrying portion 16 may include a plurality of wire apertures 86 through which the first and second anchor wires 61, 62 extend. A tip 69 may be positioned at the proximal ends 68. The tip 69 may have a bulbous construction to limit piercing of the first and second anchor wires 61, 62 into the vessel wall 24. In one embodiment, the tip 69 has a minimum dimension (e.g., diameter) that is greater than a maximum dimension (e.g., diameter) of the wire apertures 86 to limit passage of the tip 69 into the interior 46. The wire apertures 86 may be axially and circumferentially spaced apart to match axial and circumferential positions of the first and second anchor wires 61, 62 relative to the actuator wire 60.

The anchor assembly 14, when in the expanded position shown in FIGS. 6A-7C, captures a portion of a vessel wall 24 between the first and second anchor wires 61, 62 and the distal end surface 52 of the body portion 12. The vessel wall 24 may be released by advancing the actuator wire 60 distally. In some arrangements, the first and second anchor wires 61, 62 may move entirely into the suture carrying portion 16 when advancing the actuator wire 60 distally to release the vessel wall 24 so that the first and second anchor wires 61, 62 do not impede removal of the vascular closure system 10 through a vessel puncture 26.

In some arrangements, the anchor assembly 14 includes only a single anchor wire, while in other arrangements the anchor assembly 14 includes three or more anchor wires. FIGS. 14-17 show several example layouts of needle puncture locations (shown with "x") and anchor wire locations (shown with "o") relative to the body portion 12. These layouts are exemplary only and many other variations in the number and location of the needle punctures and anchor wires are possible. For example, a pair of anchor wires may be used with a single pair of needles rather than two pairs. In another example, the needle punctures may be equally spaced between each anchor wire location.

The anchor assembly 14 may have a smaller outer profile as compared to other anchor assembly configurations (e.g., see U.S. Patent Application No. 61/494,345, entitled "Large Bore Closure Device and Methods," filed on 7 Jun. 2011). The use of wire instead of other structures for the anchor and anchor actuation features may provide adequate strength and support while requiring less space. The reduced size and space requirements for the anchor assembly 14 may make it possible to reduce the size of the body portion 12 and suture carrying portion 16, and may permit the use of other shapes (e.g., circular cross-sectional shape) for the body portion 12 that promote easier insertion and removal of the vascular closure system 10 relative to the vessel puncture 26.

The first and second anchor wires 61, 62 may comprise a shape memory material such as Nitinol. The first and second anchor wires 61, 62 may have a pre-formed shape such as a J-shape or a C-shape when in a rest position. The first and second anchor wires 61, 62 may be moved or deformed into different shapes and configurations, such as a generally linear shape, during delivery though the vessel puncture 26 and storage in the suture carrying portion 16, and then return to the pre-formed shape upon being moved out of the suture carrying portion 16. FIG. 2B shows the first and second anchor wires 61, 62 having generally J-shaped construction when in the rest position.

The actuator wire 60 may comprise a shape memory material (e.g., Nitinol), stainless steel, or other alloy that can be bonded to the materials of the first and second anchor wires 61, 62.

The suture carrying portion 16 includes distal and proximal ends 70, 72, a plurality of needle receiver recesses 76, a plurality of suture recesses 78, a plurality of suture connectors 80, and first and second sutures 82, 84. The suture carrying portion 16 is connected to the delivery portion 32 of the body portion 12 at the proximal end 72. The distal locator tip 20 extends distally from the distal end 70 of the suture carrying portion 16.

The suture carrying portion 16 may also include a blood locator port 88 (see FIGS. 2D-E). The blood locator port 88 may provide an inlet for blood flow that travels through the body portion 12 to an outlet 89 (see FIG. 2A) wherein the operator can see the blood flow for a visual indication of proper insertion depth. The blood locator port 88 may be positioned proximal of the wire apertures 86 and distal of the distal end surface 52 of the delivery portion 32.

The needle receiver recesses 76 may be constructed as grooves or recesses along a length dimension of the suture carrying portion 16. Tips of the needles 18 may extend into the needle receiving recesses 76 to guide the needles 18 into the suture connectors 80.

Figure 13:
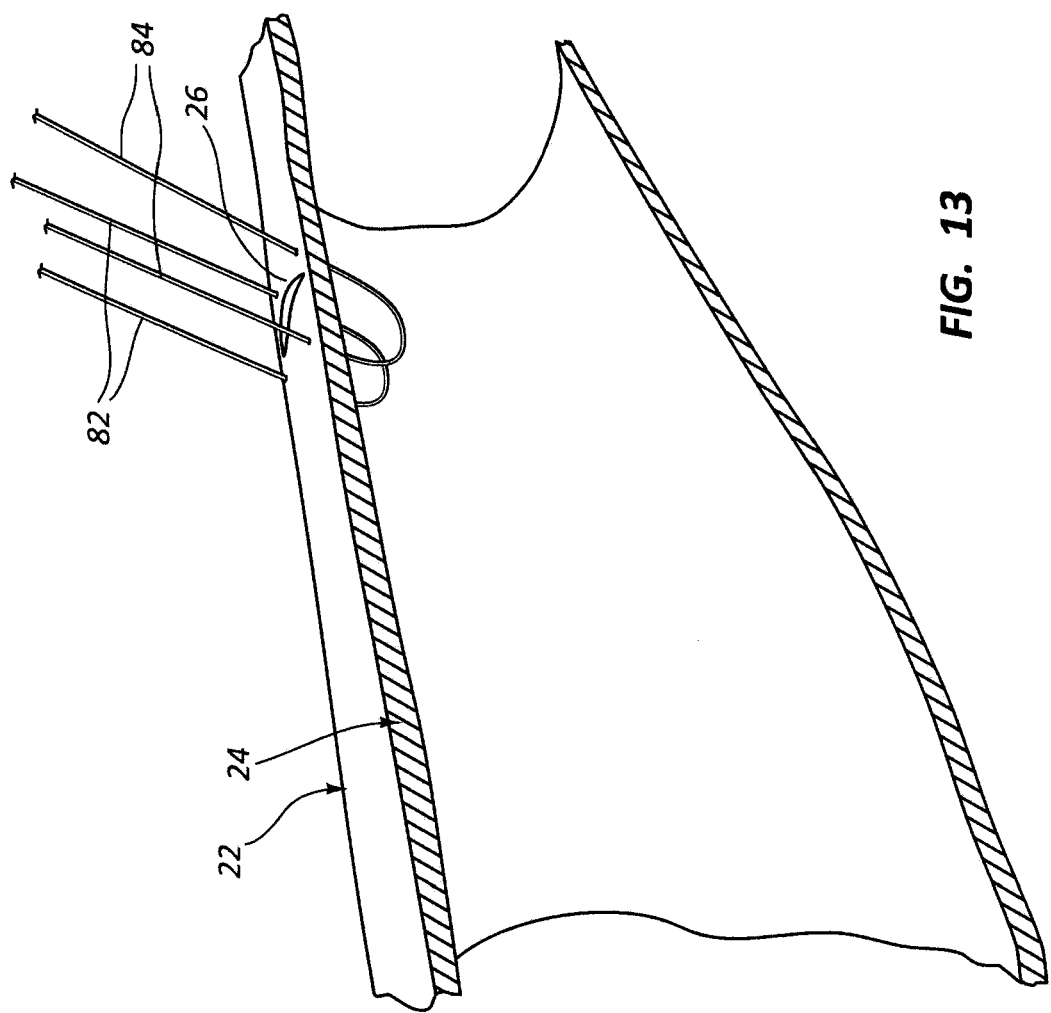
FIG. 13 illustrates the sutures extending across the vessel puncture upon removal of the vascular closure system.
Figure 14:
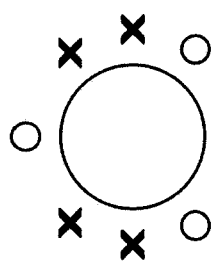
FIG. 14 is an example needle hole layout relative to positions of two anchor wires according to the embodiment of FIGS. 1-12B.
Figure 15:
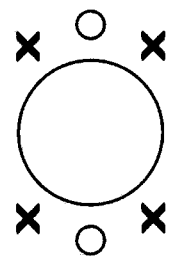
FIG. 15 is another example needle hole layout relative to positions of three anchor wires according to the present disclosure.
Figure 16:
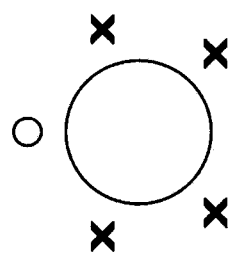
FIG. 16 is another example needle hole layout relative to positions of four anchor wires according to the present disclosure.
Figure 17:
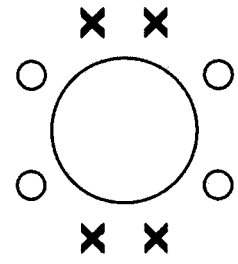
FIG. 17 is another example needle hole layout relative to positions of one anchor wire according to the present disclosure.

The vessel 22 includes a puncture 26 formed in the vessel wall 24. The needles 18 form a plurality of needle openings 29 positioned adjacent to the puncture 26. The needle openings 29 may be positioned radially outward and spaced apart from the puncture 26. Typically, the puncture 26 is generally elongate having opposing sides that define a length of the puncture and opposing ends. The first and second sutures 82, 84 may extend across the puncture 26 from one side to an opposing side as shown in FIG. 13.

The first and second sutures 82, 84 extend through the suture recesses 78 and are coupled to the suture connectors 80. The suture connectors 80 may be connected at opposing ends of the first and second sutures 82, 84. Connecting the suture connectors 80 to the needles 18 couples the first and second sutures 82, 84 to the needles 18. Typically, a separate needle 18 is connected to a separate end of one of the first and second sutures 82, 84.

The first and second sutures 82, 84 may extend at least partially within the needle receiver recesses 76 and the suture recesses 78. Additional length of the first and second sutures 82, 84 may extend along the suture carrying portion 16 proximally and extend into the body portion 12 as shown in at least FIG. 5A.

Upon connection of the needles 18 to the suture connectors 80, the needles 18 may be withdrawn proximally to pull the first and second sutures 82, 84 through the vessel wall 24 at a location adjacent to the puncture 26 (e.g., spaced radially outward from and outside of the puncture 26).

The suture connectors 80 may include a wire loop at one end for connection to a needle 18, and have a suture connection feature at an opposing end for connection to one of the first and second sutures 82, 84. Many other constructions and configurations are possible for the suture connectors 80 to provide a connection, either releasable or permanent, between the needles 18 and the first and second sutures 82, 84.

Figure 11:
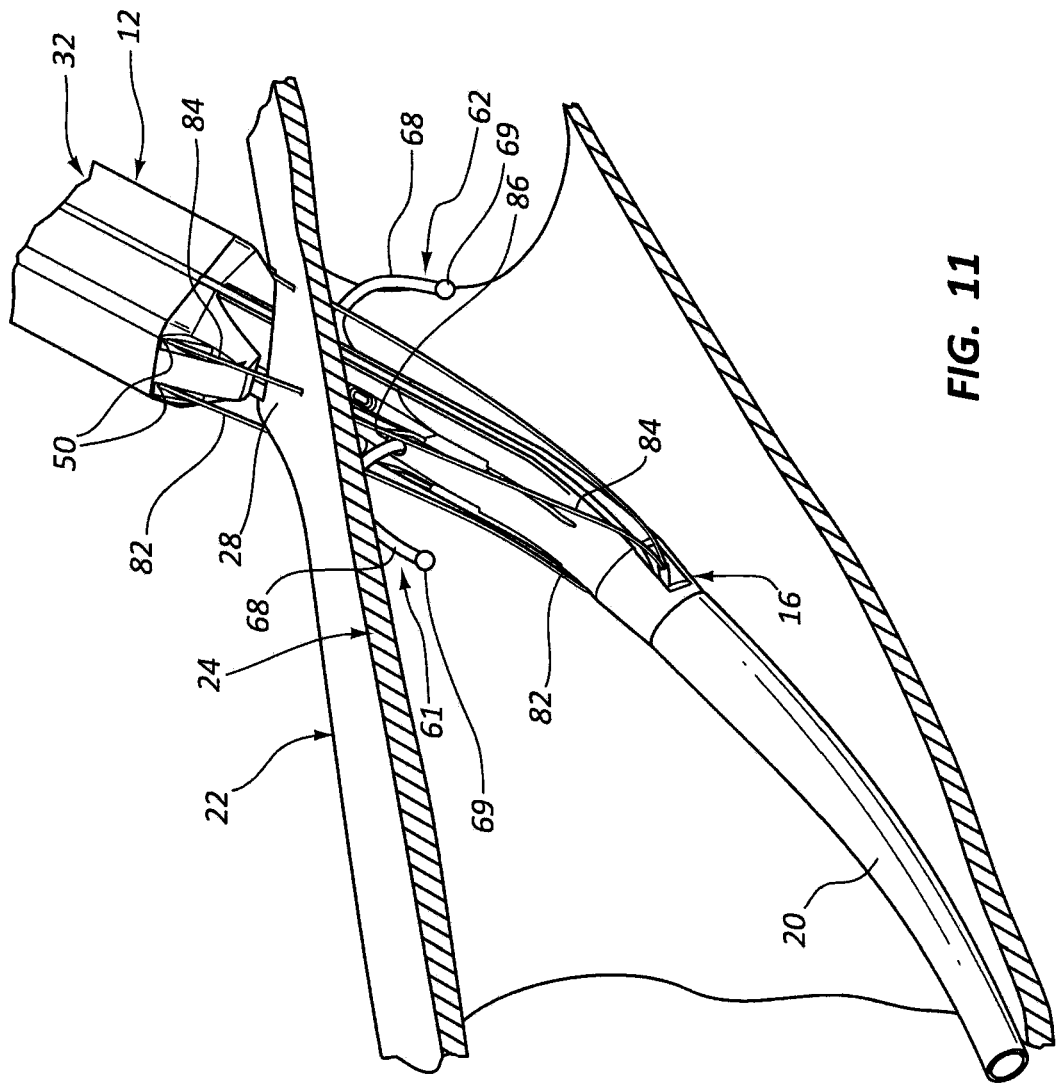
FIG. 11 is a perspective view of the distal end portion of the vascular closure system of FIG. 10A with the needles fully withdrawn and the sutures extending through the vessel wall.

The needles 18 include a distal needle tip 19. When the needles 18 are advanced by activation of the second actuator 38, the distal needle tips 19 extend through the vessel wall 24 and into the needle receiver recesses 76 (see FIG. 8A). Further advancing the needles 18 connects the distal needle tips 19 with the suture connectors 80 as shown in FIG. 9A. Withdrawing the needles 18 proximally by actuation of the second actuator 38 draws the first and second sutures 82, 84 through the needle openings 29 in the vessel wall 24 as shown in FIGS. 10A and 11. Withdrawing the vascular closure system 10 places the first and second sutures 82, 84 across a puncture 26 as shown in FIG. 13.

The anchor assembly 14 may operate to urge a portion of the vessel wall (e.g., a vessel wall aligned portion 28) into a perpendicular arrangement relative to the needles 18 as disclosed in U.S. Patent Application No. 61/494,345, entitled "Large Bore Closure Device and Methods," filed on 7 Jun. 2011, which is incorporated herein in its entirety by this reference. As the needles 18 are advanced by actuation of the second actuator 38, the needles 18 may protrude at a perpendicular angle relative to the vessel wall aligned portion 28. The needles 18 are shown in at least FIG. 8A arranged at a non-perpendicular angle relative to the remaining portions of the vessel wall 24. Typically, the body portion 12 is inserted through the vessel puncture 26 at an angle that is greater than 90°, and preferably in the range of about 100° to about 150°.

Providing the vessel wall aligned portion 28 perpendicular to the angle of advancing the needles 18 permits advancement of the needles 18 through the vessel wall concurrently and at a more precise and consistent spacing from the puncture 26 regardless of the insertion angle of the body portion 12. The improved consistency in spacing of the needle openings 29 defined by the needles 18 relative to the puncture 26 may provide improved closing and hemostasis of the puncture 26 using the first and second sutures 82, 84 that are placed through the needle openings 29. Furthermore, the consistent placement of the sutures relative to the puncture may result in less vessel scarring and less stenosis at the site of the vessel puncture. The use of multiple anchor wires with the anchor assembly 14 may help in arranging the vessel wall aligned portion 28 perpendicular to the needles 18.

An example method of positioning sutures across a vessel puncture is now described with reference to FIGS. 5A-13. A distal end portion of the vascular closure system 10 is advanced through the vessel puncture 26 to position anchor assembly 14 and suture carrying portion 16 within the vessel 22 (see FIG. 5A). A distal end of the body portion 12 is abutted against an outer surface of the vessel 22 adjacent to the vessel puncture 26. The anchor assembly 14 and needles 18 are initially maintained in retracted positions.

Referring to FIGS. 6A-7C, the first actuator 36 is operated to actuate the anchor assembly 14 into an extended or expanded position outside of hub 16 with the first and second pre-formed wires 61, 62 positioned in contact with an inner surface of the vessel wall 24 adjacent to the vessel puncture 26. The anchor assembly 14 operates by moving the actuator wire 60 proximally to move the first and second pre-formed wires 61, 62 out of the hub 16. The anchor assembly 14 captures or sandwiches the vessel wall 24 between the pre-formed wires 61, 62 and the distal end of the body portion 12 (see FIG. 7C). The anchor assembly 14 may move a vessel wall aligned portion 28 into a generally perpendicular orientation relative to a longitudinal axis of the body portion 12. The first and second pre-formed wires 61, 62 may be offset longitudinally to account for a non-perpendicular insertion angle of the vascular closure system 10 into the vessel puncture 26.

Referring to FIGS. 8A-9B, the second actuator 38 is operated to advance the needles 18 through the vessel wall aligned portion 28 and into engagement with the suture connectors 80, which are connected to the first and second sutures 82, 84. The second actuator 38 is then operated in an opposite direction to retract the needles 18. Retracting the needles 18 pulls the first and second sutures 82, 84 through the vessel wall aligned portion 28 and into the body portion 12, as shown in FIGS. 10A-B and 11.

Figure 12A:
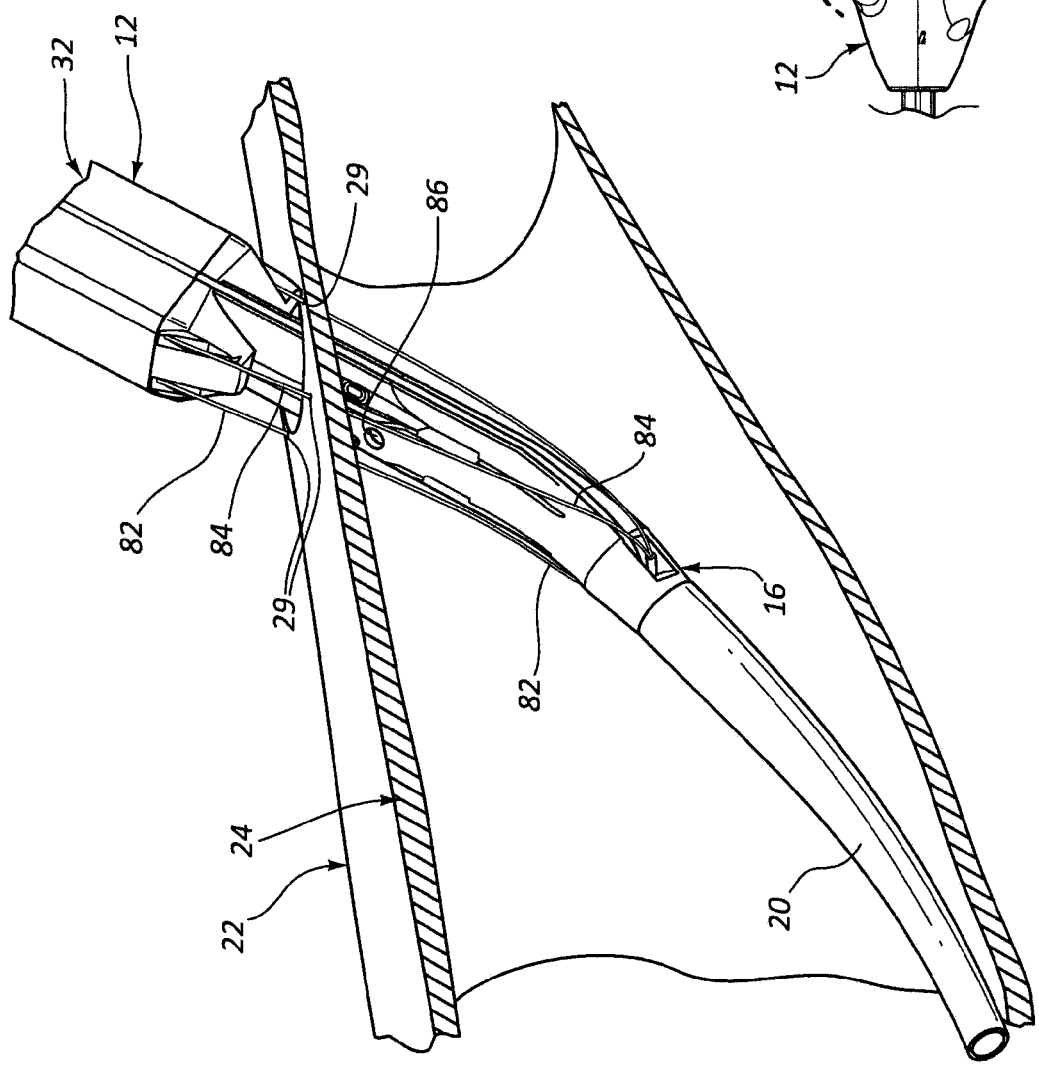
FIG. 12A is a perspective view of the distal end portion of the vascular closure system of FIG. 11 with the anchor in a retracted position.
Figure 12B:
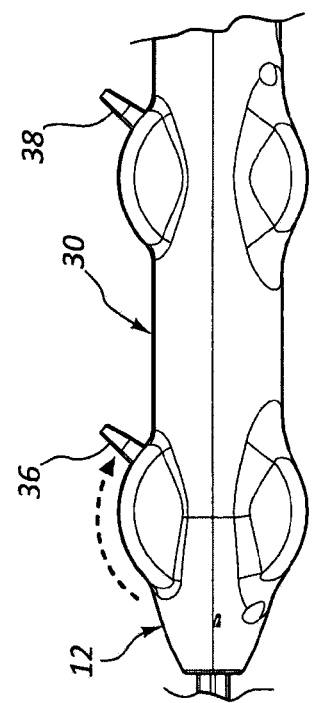
FIG. 12B shows the actuator positions of the handle portion representing a state of the distal end portion shown in FIG. 12A.

Referring to FIGS. 12A-B, the first actuator 36 is operated in an opposite direction to retract the pre-formed wires 61, 62 back into the hub 16. The actuator wire 60 may be moved distally to retract the pre-formed wires 61, 62 back into the hub 16. The vascular closure system 10 is then withdrawn from the vessel puncture 26 leaving behind the first and second sutures 82, 84 extending through the vessel wall 24 outside of the vessel puncture 26 (see FIG. 13). The first and second sutures 82, 84 may be used to seal closed the vessel puncture 26 is a further procedural step.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure system, comprising: a body portion; an anchor assembly positionable through a vessel puncture in a vessel wall of a vessel, the body portion having a distally facing surface configured to abut tissue external to the vessel wall, the anchor assembly including a hub and a wire assembly, the hub having at least one aperture defined in a sidewall thereof, and the wire assembly including an actuator member extending proximally through the body portion and hub, and at least one pre-formed wire having a proximal end, and a distal end connected to the actuator member, wherein withdrawing the actuator member extends the proximal end of the at least one pre-formed wire from a first position within the hub to a second position out of the at least one aperture to capture a portion of the vessel wall between the at least one pre-formed wire and the body portion, the at least one pre-formed wire being J-shaped; at least one suture member positioned distal of the body portion; a plurality of needles extendable from an exterior of the vessel wall through the portion of the vessel wall adjacent to the vessel puncture and into an interior of the vessel wall, the plurality of needles being configured to connect to the at least one suture member by extending through an outer surface of the hub, wherein the plurality of needles connect to the at least one suture member distal of the at least one ore-formed wire; wherein withdrawal of the plurality of needles through the portion of the vessel wall positions the at least one suture member through the portion of the vessel wall.

2. A vascular closure system according to claim 1, wherein the at least one pre-formed wire of the wire assembly includes first and second pre-formed wires arranged on opposite sides of the actuator member.

3. A vascular closure system according to claim 2, wherein the at least one aperture comprises a first aperture and a second aperture, the first aperture being formed in the hub, the second aperture being formed in the hub, wherein the first pre-formed wire extends through the first aperture and the second pre-formed wire extends through the second aperture, the first aperture being proximally spaced on the hub relative to the second aperture.

4. A vascular closure system according to claim 1, wherein the proximal end of the at least one pre-formed wire is pre-positioned in the at least one aperture.

5. A vascular closure system according to claim 1, wherein the at least one pre-formed wire includes a contact tip at the proximal end, the contact tip having a bulbous shape.

6. A vascular closure system according to claim 1, wherein the proximal end of the at least one pre-formed wire extends radially outward upon withdrawal of the actuator member.

7. A vascular closure system according to claim 1, wherein the at least one pre-formed wire is welded to the actuator member.

8. A vascular closure system according to claim 1, wherein the body portion includes a handle assembly at a proximal end thereof, and first and second actuators operable to actuate the actuator member and the plurality of needles, respectively.

9. A vascular closure device, comprising: a body portion; a hub positionable through a puncture in a vessel and having at least one aperture defined in a sidewall thereof; a wire assembly including an actuator wire extending through the body portion and hub, the actuator wire comprising a groove, the groove extending along a length dimension of the actuator wire, and at least one anchor wire having a distal end connected to the actuator wire in the groove and a proximal end movable between a first position within the hub and a second position extending out of the at least one aperture to capture a portion of a wall of the vessel between the anchor wire and the body portion upon withdrawal of the actuator wire, the body portion having a distally facing surface configured to abut tissue external to the vessel wall; first and second suture members configured to be positioned within the vessel; first and second pairs of needles operable to advance from an exterior of the vessel through the portion of the vessel adjacent to the puncture and into an interior of the vessel wall, extend through an outer surface of the hub to connect to the first and second suture members, and be withdrawn through the portion of the vessel to position the first and second suture members through the portion of the vessel, wherein the first and second pairs of needles connect to the first and second suture members distal of the at least one anchor wire.

10. A vascular closure device according to claim 9, wherein the at least one anchor wire includes first and second anchor wires configured to extend through first and second apertures defined in the sidewall of the hub.

11. A vascular closure device according to claim 9, further comprising a blood location port positioned proximal of the at least one aperture.

12. A vascular closure device according to claim 9, wherein the at least one anchor wire has a J-shape when in a rest position.

13. A vascular closure device according to claim 9, wherein the distal end of the at least one anchor wire is welded within the groove.

14. A method of positioning sutures across a vascular opening in a vessel wall, comprising: providing a vascular closure device having a body portion, an anchor assembly, at least one length of suture, and a plurality of needles, the anchor assembly including a hub, an actuator wire, and a pre-formed wire having a distal end connected to the actuator wire, the pre-formed wire being J-shaped; inserting the anchor assembly and at least one length of suture through the vascular opening; withdrawing the actuator wire to advance a proximal end of the pre-formed wire from a first position within the hub to a second position external to the hub through a sidewall of the hub; capturing a portion of the vessel wall between the pre-formed wire and a distal end of the body portion, the body portion having a distally facing surface configured to abut tissue external to the vessel wall; advancing the plurality of needles from an exterior of the vessel wall through the portion of the vessel wall adjacent to the vascular opening and into an interior of the vessel wall; connecting the plurality of needles to the at least one length of suture at a position distal to the ore-formed wire by extending the plurality of needles through an outer surface of the hub; withdrawing the plurality of needles to position the at least one length of suture through the vessel wall adjacent to the vascular opening; advancing the actuator wire to move the pre-formed wire into the hub; removing the anchor assembly through the vascular opening.

15. The method of claim 14, further comprising providing a plurality of pre-formed wires that each extend through a separate wire aperture in the sidewall of the hub.

16. The method of claim 14, wherein advancing the proximal end of the pre-formed wire positions a bend portion of the pre-formed wire in contact with the vessel wall.

17. The method of claim 14, wherein advancing the actuator wire to move the pre-formed wire into the hub includes retracting all but a proximal tip of the pre-formed wire into the hub.

18. The method of claim 14, further comprising maintaining a generally linear shape in the pre-formed wire prior to advancing the proximal end of the pre-formed wire through the sidewall of the hub, and providing a contoured shape in the pre-formed wire after advancing the proximal end through the sidewall of the hub.

19. A vascular closure system, comprising: a body portion; an anchor assembly positionable through a vessel puncture in a vessel wall of a vessel, the anchor assembly including a hub and a wire assembly, the hub having at least two apertures defined in a sidewall thereof, and the wire assembly including an actuator member extending proximally through the body portion and hub, a first pre-formed wire, and a second pre-formed wire, the first and second pre-formed wires each having a proximal end, and a distal end connected to the actuator member, wherein withdrawing the actuator member extends the proximal ends of the first and second pre-formed wires from a first position within the hub to a second position out of the at least two apertures to capture a portion of the vessel wall between the first and second pre-formed wires and the body portion; at least one suture member positioned distal of the body portion; a plurality of needles extendable from an exterior of the vessel wall through the portion of the vessel wall adjacent to the vessel puncture and into an interior of the vessel wall, the plurality of needles being configured to connect to the at least one suture member distal to the first and second pre-formed wires with the plurality of needles extending through an outer surface of the hub; wherein withdrawal of the plurality of needles through the portion of the vessel wall positions the at least one suture member through the portion of the vessel wall, and wherein the first and second pre-formed wires are arranged on opposite sides of the actuator member.

20. A vascular closure system, comprising: a body portion; an anchor assembly positionable through a vessel puncture in a vessel wall of a vessel, the anchor assembly including a hub and a wire assembly, the hub having a first aperture and a second aperture, the first and second apertures being defined in a sidewall of the hub, and the wire assembly including an actuator member extending proximally through the body portion and hub, a first pre-formed wire and a second pre-formed wire, the first and second pre-formed wires each having a proximal end, and a distal end connected to the actuator member, wherein withdrawing the actuator member extends the proximal end of the first pre-formed wire from a first position within the hub to a second position out of the first aperture to capture the vessel wall between the first pre-formed wire and the body portion, wherein withdrawing the actuator member extends the proximal end of the second pre-formed wire out of the second aperture to capture the vessel wall between the second pre-formed wire and the body portion, the first and second pre-formed wires each being J-shaped; at least one suture member positioned distal of the body portion; a plurality of needles extendable from an exterior of the vessel wall through the portion of the vessel wall adjacent to the vessel puncture and into an interior of the vessel wall, the plurality of needles being configured to connect to the at least one suture member distal to the first and second pre-formed wires; wherein withdrawal of the plurality of needles through the portion of the vessel wall positions the at least one suture member through the portion of the vessel wall, wherein the first aperture is proximally spaced on the body portion relative to the second aperture.

21. A method of positioning sutures across a vascular opening in a vessel wall, comprising: providing a vascular closure device having a body portion, an anchor assembly, at least one length of suture, and a plurality of needles, the anchor assembly including a hub, an actuator wire, and a pre-formed wire having a distal end connected to the actuator wire, the pre-formed wire being J-shaped; inserting the anchor assembly and the at least one length of suture through the vascular opening; withdrawing the actuator wire to advance a proximal end of the pre-formed wire from a first position within the hub to a second position external to the hub through a sidewall of the hub; capturing a portion of the vessel wall between the pre-formed wire and a distal end of the body portion; advancing the plurality of needles from an exterior of the vessel wall through the portion of the vessel wall adjacent to the vascular opening and into an interior of the vessel wall; connecting the plurality of needles to the at least one length of suture distal to the pre-formed wire by positioning the plurality of needles through an external surface of the hub; withdrawing the plurality of needles to position the at least one length of suture through the vessel wall adjacent to the vascular opening; advancing the actuator wire to move the pre-formed wire into the hub; removing the anchor assembly through the vascular opening; providing a plurality of pre-formed wires that each extend through a separate wire aperture in the sidewall of the hub.

22. A vascular closure device, comprising: a body portion; a hub positionable through a puncture in a vessel and having first and second apertures defined in a sidewall thereof; a wire assembly including an actuator wire extending through the body portion and hub, the actuator wire comprising a groove, the groove extending along a length dimension of the actuator wire, a first anchor wire and a second anchor wire, the first anchor wire having a distal end connected to the actuator wire in the groove and a proximal end movable from a first position within the hub to a second position extending out of the at least one aperture to capture a portion of a wall of the vessel between the anchor wire and the body portion upon withdrawal of the actuator wire, the body portion having a distally facing surface configured to abut tissue external to the vessel wall; first and second suture members configured to be positioned within the vessel; first and second pairs of needles operable to advance from an exterior of the vessel through the portion of the vessel adjacent to the puncture and into an interior of the vessel wall, connect to the first and second suture members at a position distal to the first and second anchor wires by extending through an outer surface of the hub, and be withdrawn through the portion of the vessel to position the first and second suture members through the portion of the vessel; wherein the first and second anchor wires are configured to extend through first and second apertures defined in the sidewall of the hub.

* * * * *